United States Patent
Merkel et al.

(10) Patent No.: US 12,151,997 B2
(45) Date of Patent: Nov. 26, 2024

(54) METHOD FOR PREPARING AN AMINE HYDROCHLORIDE SUSPENSION

(71) Applicant: Covestro Intellectual Property GmbH & Co. KG, Leverkusen (DE)

(72) Inventors: Michael Merkel, Düsseldorf (DE); Tim Loddenkemper, Dormagen (DE); Frank Gerhartz, Leverkusen (DE); Stefan Hirschfeld, Alpen (DE)

(73) Assignee: Covestro Intellectual Property GmbH & Co. KG, Leverkusen (DE)

( * ) Notice: Subject to any disclaimer, the term of this patent is extended or adjusted under 35 U.S.C. 154(b) by 0 days.

(21) Appl. No.: 18/143,981

(22) Filed: May 5, 2023

(65) Prior Publication Data
US 2023/0271916 A1    Aug. 31, 2023

Related U.S. Application Data

(63) Continuation of application No. 16/884,146, filed on May 27, 2020, now abandoned.

(30) Foreign Application Priority Data

Jun. 11, 2019  (EP) .................................. 19179482

(51) Int. Cl.
C07C 263/10    (2006.01)
C07C 209/74    (2006.01)
C08G 18/75     (2006.01)

(52) U.S. Cl.
CPC .......... *C07C 263/10* (2013.01); *C07C 209/74* (2013.01); *C08G 18/758* (2013.01)

(58) Field of Classification Search
None
See application file for complete search history.

(56) References Cited

U.S. PATENT DOCUMENTS

| | | |
|---|---|---|
| 3,470,227 A | 9/1969 | Hatta et al. |
| 5,136,086 A | 8/1992 | Nagata et al. |

FOREIGN PATENT DOCUMENTS

| | | |
|---|---|---|
| CA | 2010224 A1 | 8/1990 |
| CN | 104945283 A | 9/2015 |
| DE | 19957816 A1 | 6/2001 |
| EP | 0384463 A1 | 8/1990 |
| EP | 1908749 A1 | 4/2008 |
| JP | H07-252200 A | 10/1995 |
| JP | H07-258195 A | 10/1995 |
| WO | 2011108473 A1 | 9/2011 |
| WO | 2018070531 A1 | 3/2020 |

OTHER PUBLICATIONS

Acree, J. Physical & Chemical Reference Data, 2014, 43, 023102.
Copley et al., J. Am. Chem. Soc., 1941, 63, 1, 254-256.
Gould, Int. J. Pharmaceutics, 1986, 33, 201.
Haynes et al., CRC Handbook of Chemistry and Physics, 94 Ed., 2014, Section 15: Practical Laboratory Data, Laboratory Solvents and Other Liquid Reagents.

*Primary Examiner* — Sudhakar Katakam
*Assistant Examiner* — Jennifer C Sawyer
(74) *Attorney, Agent, or Firm* — The Webb Law Firm

(57) ABSTRACT

The invention relates to a method for preparing a suspension of a hydrochloride of an organic amine, comprising the following steps of (i) initially charging at least one organic solvent in a reaction vessel to form a liquid level, (ii) adding hydrogen chloride, (iii) adding the organic amine, wherein the organic amine is added below the liquid level present in the reaction vessel and steps (ii) and (iii) are at least partly carried out simultaneously. Furthermore, the present invention also relates to a method wherein the suspension obtained after step (iii) is reacted in a step (iv) with phosgene to obtain the organic isocyanate corresponding to the organic amine used, to the corresponding organic isocyanate and to the use of the organic isocyanate for producing polyisocyanates.

10 Claims, No Drawings

METHOD FOR PREPARING AN AMINE HYDROCHLORIDE SUSPENSION

CROSS REFERENCE TO RELATED APPLICATIONS

The present application is a continuation application of U.S. patent application Ser. No. 16/884,146, filed May 27, 2020, which claims priority under the Paris Convention to EP Serial No. 19179482.5, filed Jun. 11, 2019, the entire contents of which are incorporated herein by reference.

FIELD OF THE INVENTION

The present invention relates to a method for preparing a suspension of a hydrochloride of an organic amine, comprising the following steps of (i) initially charging at least one organic solvent in a reaction vessel with formation of a liquid level, (ii) adding hydrogen chloride, (iii) adding the organic amine, wherein the organic amine is added below the liquid level present in the reaction vessel and steps (ii) and (iii) are at least partly carried out simultaneously. Furthermore, the present invention also relates to a method wherein the suspension obtained after step (iii) is reacted in a step (iv) with phosgene to obtain the organic isocyanate corresponding to the organic amine used, to the corresponding organic isocyanate and to the use of this organic isocyanate for producing polyisocyanates.

BACKGROUND OF THE INVENTION

It is known that organic isocyanates can be prepared by reacting phosgene with the corresponding amines. In particular in the case of the conversion of aliphatic amines to the corresponding aliphatic isocyanates, owing to the high reactivity, high contents of undesired by-products continuously form, for example resinous, high-boiling compounds or chlorinated compounds, which form by deamination.

There has therefore been no lack of attempts to avoid or at least reduce these problems. For instance, DE 1 593 588 describes the phosgenation of xylylenediamine, in which hot phosgenation is operated with an excess of phosgene at 120 to 180° C. and a pressure of 2 to 5 atü (196 to 490 kPa). Also with this method, at most ca. 90% of the desired xylylene diioscyanate and correspondingly 10% and more of undesired by-products are formed.

EP 1 908 749 describes a variant of the method in which the amine in the so-called base phosgenation is not reacted directly with phosgene. Rather the amine is firstly reacted with hydrogen chloride to the corresponding amine hydrochloride which is then phosgenated. It should be noted that using the method according to the prior art, particularly at amine concentrations above 5% by weight in the solvent, very highly viscous suspensions are obtained which have poor flowability and pumping capability and therefore also poor stirrability. The problem is solved according to the document mentioned by operating the formation of the hydrochloride under a pressure which is at least 0.01 MPa above atmospheric pressure.

A disadvantage of such a method is operation under positive pressure which places increased requirements on the apparatus and, in the case of external leakage, the risk potential increases due to leaking gaseous hazardous substances.

DE 69 011 358 also describes a method for preparing xylylene diisocyanate in which xylylenediamine hydrochloride is reacted with phosgene in the presence of an ester as reaction solvent. The xylylenediamine in this case in one embodiment in a first step is converted to the hydrochloride at a temperature of 30° C. or less with hydrogen chloride and later phosgenated at 120 to 170°. Owing to the exothermic reaction, strong cooling is required for this procedure in order to minimize the formation of carboxamides by aminolysis of the solvent. However, it cannot be completely prevented. On the other hand, it is recommended not to lower the temperature below 0° C. such that ultimately only a narrow process window remains. Furthermore, this method is limited to the use of esters as reaction solvent wherein the previously mentioned aminolysis of the solvent occurs as a side reaction. In a phosgenation commonly preferred chlorinated aromatic solvents such as chlorobenzene or ortho-dichlorobenene which, owing to their physical and chemical properties, are particularly suitable for the preparation of isocyanates by phosgenation of the corresponding amines, cannot be used in this method.

DETAILED DESCRIPTION OF THE INVENTION

Proceeding from this prior art, the object of the present invention was to avoid the known disadvantages of the prior art, the object of the present invention particularly being to obtain even at standard pressure or in an unpressurized process and at temperatures above 30° C., a stirrable and pumpable suspension comprising the respective hydrochloride of organic amines. A further object of the invention was the economic, efficient and simple preparation of aliphatic isocyanates, preferably aliphatic diisocyanates, by phosgenation of appropriately prepared amine hydrochlorides which are in suspension.

This object was solved according to the invention by the method for preparing a suspension of a hydrochloride of an organic amine comprising the following steps:
  (i) initially charging at least one organic solvent in a reaction vessel with formation of a liquid level,
  (ii) adding the organic amine,
  (iii) adding hydrogen chloride,
wherein the organic amine is added below the liquid level present in the reaction vessel and steps (ii) and (iii) are at least partly carried out simultaneously.

The individual steps of the method according to the invention are described in detail below.

Step (i) of the method according to the invention comprises initially charging at least one organic solvent in a reaction vessel to form a liquid level.

In the context of the present invention, all organic solvents that appear suitable to a person skilled in the art for preparing hydrochlorides of organic amines can generally be used.

In accordance with the invention, an aprotic solvent is preferably used. Particularly preferably, the at least one organic solvent is selected from the group consisting of aromatic hydrocarbons, halogenated aromatic hydrocarbons, particularly chlorinated aromatic hydrocarbons, esters, ethers, halogenated hydrocarbons and mixtures thereof.

A particularly preferred aromatic hydrocarbon used in accordance with the invention is toluene.

Particularly preferred halogenated hydrocarbons used in accordance with the invention are selected from the group consisting of bromobenzene, chlorobenzene, dichlorobenzene, for example ortho-dichlorobenzene, and mixtures thereof.

The organic solvents used in accordance with the invention are very particularly preferably chlorobenzene, dichlorobenzene, for example ortho-dichlorbenzene, or mixtures thereof.

The method according to the invention can generally be carried out in any reactor deemed as suitable to a person skilled in the art. By means of steps (ii) and (iii), sufficient mixing can take place. It is evident to a person skilled in the art that the use of an additional mixing device is not essential but is an advantageous configuration.

For example, a stirred vessel is suitable as reactor. A suitable stirred vessel is described, for example, in DE 19957816 A1. It is preferably a rotationally symmetric stirred vessel with a vertical main axis. The stirred vessel can have different diameters along this main axis but is preferably essentially cylindrical. The base and top can be constructed, for example, with a dish-shaped or flat end. For temperature control, the stirred vessel can be provided with heat exchanger pipes, welded-on half-tube profiles, a double-jacketed and/or a pillow-plate system known to those skilled in the art or heat exchanger plate system, wherein the heat exchanger pipes can be configured either internally or externally.

Inlet and outlet nozzles can be positioned at any point on the wall, top and bottom of the stirred vessel. In order to fulfil the essential feature of the invention that the organic amine is added below the liquid level present in the reaction vessel, it is preferred in accordance with the invention that at least one first feed line for the organic amine or the solution of the organic amine is configured such that it flows into the reactor in the lower region. This can be achieved, for example, by means of a nozzle in the lower region of the reactor which may optionally be provided with a jet nozzle through which the organic amine or the solution of the amine can be injected into the reaction mixture. By means of the addition of the organic amine or the solution of the amine mentioned above, especially by injection, sufficient mixing of the suspension can for example already be achieved. Alternatively or in addition other mixing devices can also be used. Suitable mixing devices are, for example, stirrers, jet nozzles or ultrasound mixers. Preference is given to using a stirrer mounted on a rotating shaft. When using jet nozzles it is conceivable, for example, to withdraw part of the reaction mixture and feed it again to the reaction vessel through the jet nozzle or to add the amine or the amine solution through such a jet nozzle such that there will automatically be mixing of the reaction mixture.

In a preferred embodiment is a method for preparing a suspension of a hydrochloride of an organic amine comprising the following steps:
(i) initially charging at least one organic solvent in a reaction vessel to form a liquid level,
(ii) adding the organic amine,
(iii) adding hydrogen chloride,
wherein the organic amine is added below the liquid level present in the reaction vessel and steps (ii) and (iii) are at least partly carried out simultaneously and the resulting suspension is intermixed during the amine addition.

All other embodiments in the description and the patent claims can be combined with one another as desired and in particular with the aforementioned embodiment, unless the context clearly indicates otherwise.

In a preferred embodiment, the feed line flows into the reactor via a dip tube such that when carrying out the method according to the invention, the organic amine or the solution of the organic amine is passed through the dip tube directly into the reaction mixture.

The present invention therefore relates preferably to the method according to the invention wherein step (iii) is effected using a dip tube.

The ratio of the fill height to the diameter of the stirred vessel in accordance with the invention is preferably from 0.5:1 to 1.5:1. Higher ratios are also possible but generally also require the use of multi-stage mixing devices, preferably multi-stage stirring elements. It should be noted that by adding the reactants in the course of the method, the fill height in the vessel changes. Particularly preferably, although not mandatory, the process parameters such as initial fill level, vessel size and metering amounts are selected such that the ratio of fill height and diameter of the stirred vessel is always in the range specified above. If by the addition of the amine the range specified is breached, it is advantageous to use a multi-stage mixing device, preferably a multi-stage mixing element, such that the entire reaction mixture is well-dispersed at all times.

It is generally advantageous if the fill height of the solvent initially charged is so high that the mixing device, preferably the mixing element, is immersed in the liquid such that from the start good mixing and the highest possible heat transfer can be provided.

In accordance with the invention, the hydrogen chloride used is preferably hydrogen chloride gas. In addition, the reactor is therefore preferably provided with a second feed line for hydrogen chloride gas. Various embodiments are available for the gas feed line. If the hydrogen chloride gas is passed over, i.e. above the liquid level in the reactor, it is preferable in accordance with the invention to use a self-aspirating aeration stirrer. More preferably, the addition takes place via a nozzle in the lower region of the reactor, i.e. below the liquid level. The addition is particularly preferably via an inlet pipe which flows into the reactor below the stirrer, preferably in a gas diffuser, via which the gas already diffused as much as possible is introduced into the liquid below the stirrer. Also in this case, particular preference is given to using a self-aspirating aeration stirrer such that optimal dispersion of the hydrogen chloride gas introduced results from the external addition below the stirrer and the diffusion of the aspirated gas again from the gas space above the liquid. In a further preferred embodiment of the method according to the invention, an aeration stirrer with a hollow shaft is used for introducing the hydrogen chloride gas, wherein preferably compressed gas is fed to the hollow shaft via the second feed line.

Self-aspirating aeration stirrers in accordance with the invention are understood to mean those stirrers which are driven by a hollow shaft which have openings in the upper region, i.e. above the liquid level in the reactor, through which gas is aspirated from the gas space into the hollow shaft. The aspirated gas is transported downwards through the hollow cavity and escapes again through further openings in the stirrer blade elements below the liquid surface where it is mixed intensively with the liquid.

For addition of the organic solvent, either the first feed line can be used or alternatively a further, third, feed line. Other nozzles can be used for process monitoring, for example by means of sensors, sight glasses or sampling devices.

In addition, the reactor used in accordance with the invention is preferably equipped with a suitable stirrer, for example an aeration stirrer, paddle stirrer and/or a dynamic mixer selected from the group consisting of disperser disks, rotor-stator systems and combinations thereof.

The present invention therefore preferably relates to the method according to the invention, wherein steps (ii) and (iii) are carried out while stirring with the aid of an aeration stirrer, a paddle stirrer or a dynamic mixer selected from the group consisting of disperser disks, rotor-stator systems and combinations thereof.

The reactor preferably used in accordance with the invention furthermore also has at least one offgas line. Appropriate suitable offgas lines are known per se to those skilled in the art.

The organic solvent which is filled into the reactor in step (i) according to the invention may in this case already contain certain concentrations of the organic amine to be reacted. This concentration is, for example, 5% by weight or less, preferably 3% by weight or less, particularly preferably 2% by weight or less. If the organic amine is already present dissolved in the solvent, it is preferably present in an amount of at least 0.001% by weight. The organic amine can in accordance with the invention already be dissolved beforehand in the solvent. Alternatively, the solution is prepared only in the reaction vessel.

Particularly preferably however, the at least one organic solvent, when initially charging in the reactor, is initially free of organic amine to be reacted except for possible traces that may occur.

In the method according to the invention, the temperature of the organic solvent in the reaction vessel prior to step (ii) is preferably adjusted to −20 to 100° C., particularly preferably 20 to 90° C., especially preferably 30 to 90° C.

Step (ii) of the method according to the invention comprises the addition of hydrogen chloride.

Hydrogen chloride (HCl) is known per se to those skilled in the art and can be added in accordance with the invention as a gas or in aqueous solution as hydrochloric acid. In accordance with the invention, hydrogen chloride is preferably added as a gas, optionally in mixtures with one or more further gases, for example inert gases such as nitrogen or noble gases, preferably nitrogen. In the case that hydrogen chloride is added in a mixture with one or more inert gases, the content of hydrogen chloride in the gas mixture is preferably 5 to 99% by weight, particularly preferably 50 to 99% by weight, especially preferably 80 to 99% by weight.

Methods for preparing hydrogen chloride are known per se to those skilled in the art, for example it can be produced from the elements in a chlorine detonating gas reaction or is obtained as by-product in the chlorination of organic compounds.

Hydrogen chloride is added in gaseous form in accordance with the invention preferably at a temperature of −20° C. to 100° C., particularly preferably 10° C. to 50° C.

In the possible case according to the invention that organic amine is already in the reaction vessel, it is advantageous to initially meter in hydrogen chloride in an amount that is sufficient to fully convert the organic amine initially charged to the corresponding hydrochloride, before starting metering in further organic amine according to step (iii).

It is also possible in accordance with the invention to begin the metering in of the hydrogen chloride at the same time as metering in the organic amine (step (iii)). Owing to the higher risk of agglomerate formation in this embodiment, either the hydrogen chloride gas can be metered in in accordance with the invention in higher excess based on the amine, or after addition of the amine is complete further hydrogen chloride is added until the total amount of organic amine has been converted to the hydrochloride. In this case, a higher excess preferably signifies an equivalence ratio of HCl to amine of from 1.1:1 to 20, particularly preferably from 1.2:1 to 5:1.

The hydrogen chloride gas is preferably introduced below the liquid level in the reactor. The hydrogen chloride gas is particularly preferably introduced below the mixing device, preferably the mixing element, especially preferably the addition being carried out through a gas diffuser below the mixing device, preferably the mixing element.

The gas feed device is preferably positioned such that, even in the case of thrombus formation, the feed always takes place in the liquid and not in the gas space.

Step (iii) of the method according to the invention comprises the addition of the organic amine.

The organic amines used can in principle be all compounds having primary amino groups known to those skilled in the art. However, in accordance with the invention, preference is given to those compounds having at least 2, particularly preferably 2 or 3 $NH_2$ groups which may be bonded aliphatically, cyclopaliphatically, araliphatically or aromatically. In accordance with the invention, very particular preference is given to those amines having 2 aliphatically, cycloaliphatically and/or araliphatically bonded $NH_2$ groups.

Suitable aromatic amines are, for example, selected from the group consisting of pure isomers or isomeric mixtures of diaminotoluene, diaminodimethylbenzene, diaminonaphthalene, diaminobenzene, diaminodiphenylmethane and mixtures thereof. Particularly preferred aromatic amines are selected from the group consisting of 2,4-diaminotoluene, 2,6-diaminotoluene, 1,5-diaminonaphthalene, p-phenylenediamine and mixtures thereof.

Suitable aliphatic, cycloaliphatic or araliphatic amines are, for example, selected from the group consisting of 1,4-diaminobutane, 1,5-diaminopentane (PDA), 1,6-diaminohexane (HDA), 1,11-diaminoundecane, 1-amino-3,5,5-trimethyl-5-aminomethylcyclohexane (IPDA), bis(p-aminocyclohexyl)methane (PACM), 1,5-diamino-2-methylpentane, 2,5-diamino-2,5-dimethylhexane, 1,4-diaminocyclohexane, 2,4-hexahydrotoluylenediamine, 2,6-hexahydrotoluylenediamine (H6TDA), 1,3-bis(aminomethyl)benzene (m-XDA), 1,4-bis(aminomethyl)benzene (p-XDA), isomers of bis(aminomethyl)cyclohexane (H6-XDA), tetramethylxylylenediamine (TMXDA), isomeren of bis(aminomethyl)norbornane (NBDA), neopentanediamine, 2,4,4-trimethylhexamethylenediamine, 2,2,4-trimethylhexamethylenediamine and mixtures thereof.

The present invention therefore preferably relates to the method according to the invention, wherein the organic amine is selected from the group consisting of aromatic amines, preferably selected from the group consisting of pure isomers or isomeric mixtures of diaminotoluene, diaminodimethylbenzene, diaminonaphthalene, diaminobenzene, diaminodiphenylmethane and mixtures thereof, aliphatic, cycloaliphatic or araliphatic amines, preferably selected from the group consisting of 1,4-diaminobutane, 1,5-diaminopentane (PDA), 1,6-diaminohexane (HDA), 1,11-diaminoundecane, 1-amino-3,5,5-trimethyl-5-aminomethylcyclohexane (IPDA), bis(p-aminocyclohexyl)methane (PACM), 1,5-diamino-2-methylpentane, 2,5-diamino-2,5-dimethylhexane, 1,4-diaminocyclohexane, 2,4-hexahydrotoluylenediamine, 2,6-hexahydrotoluylenediamine (H6TDA), 1,3-bis(aminomethyl)benzene (m-XDA), 1,4-bis(aminomethyl)benzene (p-XDA), isomers of bis(aminomethyl)cyclohexane (H6-XDA), tetramethylxylylenediamine (TMXDA), isomers of bis(aminomethyl)norbornane (NBDA), neopentanediamine, 2,4,4-trimethylhexamethylenediamine, 2,2,4-trimethylhexamethylenediamine and mixtures thereof.

In accordance with the invention, especially preferred organic amines are selected from the group consisting of 1,5-diaminopentane (PDA), 1,6-diaminohexane (HDA), 1-amino-3,5,5-trimethyl-5-aminomethylcyclohexane (IPDA), 1,3-bis(aminomethyl)benzene (m-XDA), isomers of bis(aminomethyl)cyclohexane (H6-XDA), isomers of bis(aminomethyl)norbornane (NBDA), 2,4,4-trimethylhexamethylenediamine, 2,2,4-trimethylhexamethylenediamine and mixtures thereof.

In step (iii) of the method according to the invention, the organic amine or the mixture comprising more than one organic amine can be added without solvent or dissolved in at least one solvent. Suitable solvents are all solvents known per se to those skilled in the art which are inert to the prevailing reaction conditions. The at least one organic amine is preferably dissolved in the same solvent or solvent mixture which is initially charged in the reactor. Particularly preferred solvents to dissolve the at least one organic amine are therefore selected from the group consisting of aromatic hydrocarbons, halogenated aromatic hydrocarbons, particularly chlorinated aromatic hydrocarbons, esters, ethers and halogenated hydrocarbons and mixtures thereof. Particularly preferred aromatic hydrocarbons used in accordance with the invention are selected from the group consisting of toluene, bromobenzene, chlorobenzene, dichlorobenzene, for example ortho-dichlorobenzene, and mixtures thereof. In accordance with the invention, particular preference is given to using chlorobenzene, dichlorobenzene or mixtures thereof.

In accordance with the present method, the organic amine is preferably used dissolved in at least one solvent, preferably selected from the group consisting of aromatic hydrocarbons, halogenated aromatic hydrocarbons, particularly chlorinated aromatic hydrocarbons, esters, ethers and halogenated hydrocarbons and mixtures thereof, especially selected from the group consisting of toluene, bromobenzene, chlorobenzene, dichlorobenzene, for example ortho-dichlorobenzene, and mixtures thereof.

The organic amine is preferably added as a solution in an inert solvent. The concentration of the organic amine in the solvent is preferably 5 to 50% by weight, particularly preferably 10 to 30% by weight, based in each case on the solution. In this manner, in accordance with the invention, the formation of agglomerates due to local superelevated concentrations of the organic amine can be further minimized.

A feature essential to the invention is that the organic amine is added below the liquid level present in the reaction vessel, wherein the input is preferably effected via a dip tube. In accordance with the invention, below the liquid level present in the reaction vessel signifies that preferably the feed is effected continuously into the reaction mixture in the reaction vessel.

A further feature essential to the invention is that steps (ii) and (iii) are at least partly, preferably completely, carried out simultaneously. In the context of the present invention, at least partly signifies that the addition is effected simultaneously preferably to an extent of 40 to 100%, particularly preferably 80 to 99%, particularly preferably 80 to 95%. That means that this mass fraction of the total amount of the organic amine to be added is passed into the reactor while also hydrogen chloride is passed into the reactor in order to react with the organic amine to the corresponding hydrochloride. However, it is also possible in accordance with the invention that organic amine or hydrogen chloride are partly initially charged and then the simultaneous addition is carried out.

The metering in of the organic amine and hydrogen chloride is carried out in a preferred embodiment of the method according to the invention such that the hydrogen chloride is added in stoichiometric excess based on the amino groups of the organic amine metered in. In this manner, it is prevented that the organic amine accumulates to undesired high concentrations and a finely divided suspension is obtained.

While both reactants are metered in, the substance streams of hydrogen chloride and organic amine are preferably at an equivalence ratio to each other of from 1:1 to 10:1, particularly preferably 1:1 to 3:1, especially preferably 1.05:1 to 1.8:1.

The total amount of hydrogen chloride metered in is preferably sufficient to fully convert the organic amine, i.e. to an extent of more than 99%, preferably more than 99.5% and particularly preferably more than 99.9% to the hydrochloride.

The end concentration of hydrochloride in the reaction mixture is preferably 5 to 30% by weight, particularly preferably 7 to 25% by weight, especially preferably 10 to 20% by weight. The value for the end concentration of hydrochloride is calculated from the mass of the organic amine present in the reactor under consideration of the molecular weight increase due to formation of the hydrochloride, wherein a complete conversion of all amino groups to the corresponding ammonium chloride groups is assumed, based on the total mass of the reactor content. In the preferred concentration range specified in accordance with the invention, a particularly advantageous compromise of high efficiency of the method and good handling of the suspension is available.

After the preparation of the hydrochloride according to the invention comprising steps (i), (ii) and (iii), the suspension obtained after step (iii) is preferably reacted in a step (iv) with phosgene to obtain the organic isocyanate corresponding to the organic amine used.

The present invention therefore preferably relates to the method according to the invention wherein the suspension obtained after step (iii) is reacted in a step (iv) with phosgene to obtain the organic isocyanate corresponding to the organic amine used.

The suspension of hydrochloride obtained by the method according to the invention can be subsequently converted to the corresponding isocyanate by reaction with phosgene. For this purpose, the suspension can either remain in the reaction vessel or be transferred to another reaction vessel.

For the phosgenation step, the same types of reaction vessels can be used as previously described for the preparation of the hydrochloride suspension. The suspension is then heated to a temperature of 120 to 200° C. with introduction of phosgene, optionally diluted with an inert gas or gas mixture, for example nitrogen or noble gases. Particularly for less thermally stable isocyanates, it is preferable that this temperature is 120 to 170° C., particularly preferably 120 to 160° C.

In accordance with the invention therefore, the phosgenation is preferably carried out at a temperature of 120 to 170° C., particularly preferably 130 to 160° C. The phosgenation can be carried out either at atmospheric pressure or at positive pressure. The pressure is preferably 1 to 10 bar(a), particularly preferably 1 to 5 bar(a).

Phosgene is preferably used in stoichiometric excess for the phosgenation. Higher excesses act positively on the reaction rate and therefore the duration of the reaction but naturally impair the economy of the method. Typically therefore the reaction is carried out using a phosgene excess of 100 to 500%, preferably 150 to 300%. Optionally, an inert gas can also be introduced into the reaction mixture.

The phosgene is added to the hydrochloride suspension, preferably by introducing gaseous phosgene. The phosgene is preferably introduced below the liquid level in the reactor. The phosgene is particularly preferably introduced below the mixing device, especially preferably the addition being carried out through a gas diffuser below the mixing device. Aeration stirrers with hollow shaft are preferably used as mixing device as already described above.

In an alternative embodiment, the phosgene is introduced into the reactor as a solution in an inert solvent. The same solvent is preferably used for this purpose in which the suspension of the hydrochloride is also present.

In a further alternative embodiment, it is also possible to initially charge a phosgene solution in a reaction vessel and to add the hydrochloride suspension prepared according to the invention to this solution.

It can be advantageous to flush the feed lines for amine and/or hydrogen chloride, before and/or after the reaction, with solvent and/or inert gas, preferably nitrogen.

After completion of the reaction, i.e. at largely complete conversion, i.e. preferably 80 to 99%, particularly preferably 90 to 99% of the theoretical value, of the hydrochloride to the corresponding isocyanate, excess phosgene and hydrogen chloride are preferably removed from the reaction mixture. For this purpose, generally an inert gas, preferably nitrogen, is passed through the reaction mixture. Optionally, phosgene and hydrogen chloride can be removed or be assisted also by applying a negative pressure. If needed, filtration can be carried out in order to remove solids possibly present such as unreacted hydrochloride particles.

Subsequently, the reaction product is preferably processed according to methods known from the prior art, i.e. it is preferably purified in a multi-stage vacuum distillation. In particular, in this distillative processing, the isocyanate is freed from solvent, chlorinated by-products and higher-boiling residues.

Since solvents are preferably used for preparing isocyanates which have a lower boiling point than the respective isocyanate, the distillation preferably comprises solvent removal. In this distillation step, low-boiling secondary components, particularly chlorinated low-boiling secondary components, are removed. The solvent can, optionally after further purification steps, be fed back again into the process.

In addition, such a purification process preferably comprises a purification by distillation to separate the isocyanate from high-boiling residue. All distillation steps are preferably carried out under reduced pressure in order to reduce the temperatures required for distillation and thus the thermal stress on the product. In particular, this distillation step is carried out at a pressure of 5 to 50 mbar(a) and a bottom temperature of 90 to 250° C., preferably 120 to 170° C. When necessary, in order to suppress the formation of uretdiones in the distillate, the distillate is preferably cooled as rapidly as possible to temperatures below 90° C., preferably below 80° C. This can be achieved, for example, by quenching the distillate, especially by mixing with product already cooled.

After step (iv) of the method according to the invention, the organic isocyanate is preferably obtained, in particular 1,5-diisocyanatopentane (PDI), 1,6-diisocyanatohexane (HDI), 1-isocyanato-3,5,5-trimethyl-5-isocyanatomethylcyclohexane (IPDI), 1,3-bis(isocyanatomethyl)benzene (m-XDI), isomers of bis(isocyanatomethyl)cyclohexane (H6-XDI), isomers of bis(iscyanatomethyl)norbornane (NBDI), 2,4,4-trimethylhexamethylenediamine, 2,2,4-trimethylhexamethylenediamine or mixtures thereof, in pure form, i.e. at a purity of at least 99.5%.

The present invention also relates to an organic isocyanate obtainable by the method according to the invention. In particular, the present invention relates to an organic isocyanate obtainable by the method according to the invention selected from the group consisting of 1,5-diisocyanatopentane (PDI), 1,6-diisocyanatohexane (HDI), 1-isocyanato-3,5,5-trimethyl-5-isocyanatomethylcyclohexane (IPDI), 1,3-bis(isocyanatomethyl)benzene (m-XDI), isomers of bis(isocyanatomethyl)cyclohexane (H6-XDI), isomers of bis(isocyanatomethyl)norbornane (NBDI), 2,4,4-trimethylhexamethylenediamine, 2,2,4-trimethylhexamethylenediamine and mixtures thereof.

The present invention also relates to the use of the organic isocyanates according to the invention for producing polyisocyanates comprising isocyanurate groups, polyisocyanates comprising uretdione groups, polyisocyanates comprising biuret groups, polyisocyanates comprising urethane or allophanate groups, polyisocyanates comprising oxadiazinetrione groups or iminooxadiazinedione groups and/or uretonimine-modified polyisocyanates.

Such polyisocyanates based on organic isocyanates according to the invention or the organic isocyanate itself can be used, for example, for producing plastics comprising urethane, thiourethane, isocyanurate, amide and/or urea groups by the polyisocyanate polyaddition process. Such polyisocyanate mixtures are particularly used for producing light-stable polyurethane lacquers and coatings.

EXAMPLES

Comparative Example 1

A stirred vessel composed of glass with a heat-controlled jacket and a length-to-internal diameter ratio of 1.2 was equipped with a paddle stirrer, where the stirrer paddle diameter to internal diameter of the reactor was at a ratio of 0.75. The stirred vessel was charged with 5 g of monochlorobenzene. At the same time 1 kg of m-xylylenediamine in 4 kg of o-dichlorobenzene was initially charged in a raw material reservoir. At the same time, with stirring at atmospheric pressure, hydrogen chloride gas was passed into the reactor via a gas inlet tube and the amine solution provided in the raw material reservoir was added, wherein the amine solution was added from above, i.e. above the liquid level in the stirred vessel. The metered addition was effected over 2 h at a metered addition rate of 321 g/h for hydrogen chloride and 2.5 kg/h for the amine solution. The amine feed was then terminated and hydrogen chloride was further fed for 60 min at a metered addition rate of 150 g/h. The temperature in the stirred vessel during the entire procedure was maintained at 25° C. by means of the heat-controlled jacket.

Thick sticky deposits were evident on the wall of the stirred vessel, on the stirrer and on the inlet nozzle of the amine solution. The reaction mixture obtained comprised large solid agglomerates with diameters>1 mm, which settled out. The resulting reaction mixture was therefore no longer suitable for being stirred or pumped.

Example 2 (According to the Invention)

The stirred vessel according to comparative example 1 was modified so that now the amine solution was fed directly into the reaction mixture through a dip tube and therefore below the liquid level. In addition, after termination of the amine addition, hydrogen chloride was further fed for 30 minutes at a metered addition rate of 150 g/h. The experiment of comparative example 1 was repeated under otherwise unmodified conditions. The temperature in the stirred vessel was maintained at 25° C. by means of the heat-controlled jacket.

There were only minor deposits on the wall of the stirred vessel. The stirrer and the dip tube for feeding were free of adhesions. The resulting suspension could be stirred and pumped but still comprised relatively large solid particles but the size of which was below 1 mm in diameter.

Example 3 (According to the Invention)

For a further experiment, the stirred vessel was again modified by replacing the paddle stirrer with an aeration stirrer. The experiment of example 2 (according to the invention) was repeated, wherein now the hydrogen chloride was introduced through the aeration stirrer. In addition, the reactor was preheated to 35° C. by the heat-controlled jacket and was maintained at this temperature during addition of the reactants. After completion of the experiment, only small deposits were again observed on the wall of the stirred vessel, while the stirrer and the dip tube were free of deposits. The resulting suspension was homogeneous, finely-divided and could be stirred and pumped.

Example 4 (According to the Invention)

The experiment of example 3 (according to the invention) was repeated, wherein contrary to the conditions in example 3, the reactor was preheated to 80° C. by the heat-controlled jacket and was maintained at this temperature during the addition of the reactants. This again resulted in a homogeneous finely-divided, stirrable and pumpable suspension and also deposits on the wall of the reactor could be further minimized.

Example 5 (According to the Invention)

The method was as in example 4 but an isomeric mixture of 2,2,4- and 2,4,4-trimethylhexamethylenediamine was used as amine. This was placed in the raw material reservoir as a 20% by weight solution in monochlorobenzene. The temperature was again regulated to 80° C. and the metered addition rate was 2.5 kg/h for the amine solution and 275 g/h for hydrogen chloride. After 2 hours, the metered addition of amine was terminated and hydrogen chloride was further fed for 30 min at a metered addition rate of 100 g/h. A homogeneous finely-divided, stirrable and pumpable suspension was again obtained. Deposits did not occur.

Comparative Example 6

In deviation from example 5, in comparative example 6 the reactor was initially charged with 10 kg of a 10% solution of the isomeric mixture of 2,2,4- and 2,4,4-trimethylhexamethylenediamine in monochlorobenzene and temperature-controlled at 25° C. Then, with vigorous stirring, hydrogen chloride gas was introduced over 2.5 h at a metered addition rate of 275 g/h. There were heavy deposits on walls and stirrers and relatively large solid agglomerates with diameters>1 mm formed, which settled on the bottom of the vessel.

Example 7 (According to the Invention)

In the raw material reservoir, 900 g of isomeric mixture of 2,2,4- and 2,4,4-trimethylhexamethylenediamine were initially charged in 4 kg of monochlorobenzene. In the stirred vessel, a further 100 g of the amine were initially charged in 5 kg of monochlorobenzene. The reaction mixture was heated to 60° C. and while stirring initially 70 g of hydrogen chloride were added through the aeration stirrer. Only then was the simultaneous metered addition of the amine solution and further hydrogen chloride begun. The metered addition rates were 2.45 kg/h for the amine solution, which was fed in accordance with the invention through a dip tube below the liquid level and 250 g/h for the hydrogen chloride. After 2 hours, the addition of amine was terminated and hydrogen chloride was further metered in for 30 min at a reduced metered addition rate of 100 g/h. After completion of the experiment, only small deposits were again observed on the wall of the stirred vessel, while the stirrer and the dip tube were free of deposits. The resulting suspension was homogeneous, finely-divided and could be stirred and pumped.

Example 8 (According to the Invention)

In a stirred vessel modified as described in example 3, 5000 g of monochlorobenzene were initially charged and the reactor was preheated to 70° C. by means of the heat-controlled jacket and maintained at this temperature during addition of the reactants. A solution of 1000 g of aniline in 4000 g of monochlorobenzene was added as amine solution from the raw material reservoir via the dip tube. Hydrogen chloride gas was introduced through the aeration stirrer. The metered addition rates were 2 kg/h for the amine solution and 500 g/h for hydrogen chloride. After 2.5 h all the amine had been added and further hydrogen chloride was introduced for 30 minutes at a metered addition rate of 100 g/h. A homogeneous finely-divided, stirrable and pumpable suspension was obtained. Deposits did not occur.

Example 9 (According to the Invention)

The experiment of example 5 was repeated wherein, instead of o-dichlorobenzene, in this case monochlorobenzene was initially charged and the amine solution was added in o-dichlorobenzene. Other conditions remained unchanged. A homogeneous finely-divided, stirrable and pumpable suspension was again obtained. Deposits did not occur.

The invention claimed is:

1. A method for preparing a suspension of a hydrochloride of an organic amine, comprising the following steps:
   (i) initially charging at least one organic solvent in a reaction vessel to form a liquid level,
   (ii) adding hydrogen chloride,
   (iii) adding the organic amine,
   wherein the organic amine is added below the liquid level present in the reaction vessel and steps (ii) and (iii) are at least partly carried out simultaneously,
   where the organic amine is selected from the group consisting of 1,3-bis(aminomethyl)benzene (m-XDA),
   wherein steps (ii) and (iii) are carried out while stirring with the aid of a stirring device comprising an aeration stirrer, paddle stirrer, or a dynamic mixer selected from the group consisting of disperser disks, rotor-stator systems and combinations thereof,
   wherein hydrogen chloride is added as a gas either via an aeration stirrer or via a gas diffuser located below the stirring device.

2. The method according to claim 1, wherein the temperature of the organic solvent in the reaction vessel prior to step (ii) is adjusted to −20 to 100° C.

3. The method according to claim 1, wherein step (iii) is carried out using a dip tube.

4. The method according to claim 1, wherein the at least one organic solvent is selected from the group consisting of aromatic hydrocarbons, halogenated aromatic hydrocarbons, esters, ethers, halogenated hydrocarbons and mixtures thereof.

5. The method according to claim 1, wherein the organic amine is added as a solution in an inert solvent.

6. The method according to claim 5, wherein the concentration of the organic amine in the solvent is 5 to 50% by weight, based on weight of the solution.

7. The method according to claim 1, wherein the substance streams of hydrogen chloride and organic amine during steps (ii) and (iii) are in an equivalence ratio to each other of from 1:1 to 10:1.

8. The method according to claim 1, wherein the end concentration of hydrochloride in the reaction mixture is 5 to 30% by weight.

9. The method according to claim 1, wherein the suspension obtained after step (iii) is reacted in a step (iv) with phosgene to obtain an organic isocyanate corresponding to the organic amine used.

10. The method according to claim 1, wherein the stirring device is selected from the group consisting of aeration stirrers and self-aspirating aeration stirrers.

* * * * *